US009632190B2

(12) United States Patent
Stowe et al.

(10) Patent No.: US 9,632,190 B2
(45) Date of Patent: Apr. 25, 2017

(54) NEUTRON IMAGING SYSTEMS UTILIZING LITHIUM-CONTAINING SEMICONDUCTOR CRYSTALS

(71) Applicants: Ashley C. Stowe, Knoxville, TN (US); Arnold Burger, Nashville, TN (US)

(72) Inventors: Ashley C. Stowe, Knoxville, TN (US); Arnold Burger, Nashville, TN (US)

(73) Assignees: Consolidates Nuclear Security, LLC, Oak Ridge, TN (US); Fisk University, Nashville, TN (US)

( * ) Notice: Subject to any disclaimer, the term of this patent is extended or adjusted under 35 U.S.C. 154(b) by 540 days.

(21) Appl. No.: 14/230,372

(22) Filed: Mar. 31, 2014

(65) Prior Publication Data

US 2016/0370477 A1 Dec. 22, 2016

Related U.S. Application Data

(63) Continuation-in-part of application No. 13/658,591, filed on Oct. 23, 2012, now Pat. No. 9,334,581.

(51) Int. Cl.
| | |
|---|---|
| *G01N 23/04* | (2006.01) |
| *G01T 3/08* | (2006.01) |
| *C30B 11/12* | (2006.01) |
| *C30B 11/06* | (2006.01) |

(Continued)

(52) U.S. Cl.
CPC ............... *G01T 3/08* (2013.01); *C30B 11/06* (2013.01); *C30B 11/12* (2013.01); *C30B 29/46* (2013.01); *G01N 23/046* (2013.01); *G01N 23/05* (2013.01)

(58) Field of Classification Search
CPC ......... G01N 23/046; G01N 23/06; G01T 3/08
See application file for complete search history.

(56) References Cited

U.S. PATENT DOCUMENTS

| | | | |
|---|---|---|---|
| 7,687,780 | B2 | 3/2010 | Bell et al. |
| 2004/0251419 | A1* | 12/2004 | Nelson .................... G01T 1/243 250/370.09 |

(Continued)

OTHER PUBLICATIONS

O. Balachninaite, L. Petraviciute, M. Maciulevicius, V. Sirutkaitis, L. Isaenko, S. Lobanov, A. Yelisseyev, J.-J. Zondy; Absorptance and scattering losses measurements of the mid-infrared nonlinear crystals LiInSe2 and LiInS2 in the IR range.; ISSN 1392-2114 ULTRAGARSAS Nr.3(60). 2006.

(Continued)

*Primary Examiner* — Mark R Gaworecki
(74) *Attorney, Agent, or Firm* — Clements Bernard Walker PLLC; Christopher L. Bernard; Lawrence A. Baratta, Jr.

(57) ABSTRACT

A neutron imaging system, including: a plurality of Li-III-$VI_2$ semiconductor crystals arranged in an array, wherein III represents a Group III element and VI represents a Group VI element; and electronics operable for detecting and a charge in each of the plurality of crystals in the presence of neutrons and for imaging the neutrons. Each of the crystals is formed by: melting the Group III element; adding the Li to the melted Group III element at a rate that allows the Li and Group III element to react, thereby providing a single phase Li-III compound; and adding the Group VI element to the single phase Li-III compound and heating. Optionally, each of the crystals is also formed by doping with a Group IV element activator.

22 Claims, 4 Drawing Sheets

(51) Int. Cl.
*C30B 29/46* (2006.01)
*G01N 23/05* (2006.01)

(56) References Cited

U.S. PATENT DOCUMENTS

2007/0080301 A1* 4/2007 Bell .......................... G01T 1/24
250/370.12
2010/0327170 A1* 12/2010 Ivan ....................... G01T 3/085
250/370.05

OTHER PUBLICATIONS

L. Isaenko, A. Yelisseyev, S. Lobanov, A. Titov, V. Petrov, J.-J. Zondy, P. Krinitsin, A. Merkulov, V. Vedenyapin, J. Smironova; "Growth and properties of LiGaX2 (X-S, Se, Te) single crystals for nonlinear optical applications in the mid-IR"; Crys. Res. Technol. 38, No. 3-5, 379-387 (2003) / DO1 10.1002/crat.200310047.; 2003 WILEY-VCH Verlag GmbH & Co. KGaA, Wenheim 0232-1300/03/3-504-0379.

L. Isaenko, P. Krinitsin, V. Vedenyapin, A. Yelisseyev, A. Merkulov, J.-J. Xondy, and V. Petrov; "LiGaTe2: A New Highly Nonlinear Chalcopyrite Optical Crystal for the Mid-IR"; Crystal Growth & Design, vol. 5. No. 4 1325-1329, 2005.

* cited by examiner

NEUTRON IMAGING SYSTEMS UTILIZING LITHIUM-CONTAINING SEMICONDUCTOR CRYSTALS

CROSS-REFERENCE TO RELATED APPLICATION

The present patent application/patent is a continuation-in-part (CIP) of U.S. patent application Ser. No. 13/658,591, filed on Oct. 23, 2012, and entitled "METHODS FOR SYNTHESIZING SEMICONDUCTOR QUALITY CHALCOPYRITE CRYSTALS FOR NONLINEAR OPTICAL AND RADIATION DETECTION APPLICATIONS AND THE LIKE," the contents of which are incorporated in full by reference herein.

STATEMENT REGARDING FEDERALLY SPONSORED RESEARCH OR DEVELOPMENT

The U.S. Government has rights to the present disclosure pursuant to Contract No. AC05-00OR22800 between the U.S. Department of Energy and Babcock and Wilcox Technical Services Y-12, LLC.

FIELD OF THE DISCLOSURE

The present disclosure relates generally to methods for synthesizing semiconductor quality chalcopyrite crystals for nonlinear optical and radiation detection applications and the like. More specifically, the present disclosure relates to methods for synthesizing a semiconductor detector of ionizing electromagnetic radiation, neutrons, and energetic charged particles. Finally, the present disclosure relates to neutron imaging systems utilizing Li chalcopyrite crystals synthesized by the methods described herein.

BACKGROUND OF THE DISCLOSURE

The present state-of-the-art in semiconductor radiation detection is silicon diodes, high purity germanium (cooled by liquid nitrogen), and compound semiconductors, such as cadmium zinc telluride (CZT) and mercuric iodide. Each of these materials has one or more significant drawbacks related to its use. Silicon has a low atomic number and is therefore primarily useful for the detection of energetic charged particles and atomic x-rays emitted by low atomic number elements. Germanium has a higher atomic number but, because of its low band gap energy, must be cooled by liquid nitrogen in a bulky, expensive, and potentially dangerous cryogenic system in order to reduce thermally generated noise. Compound semiconductors, such as CZT and mercuric iodide, have sufficiently high band gap energy to be useful at or near room temperature. However, CZT has been plagued by production problems, resulting in polycrystalline ingots with twins, inclusions, and grain boundary defects. These defects can never be completely removed and are a consequence of CZT being a solid solution, rather than a true compound. The result is that spectroscopy grade crystals must be mined from bulk material. Mercuric iodide suffers from low carrier mobility, short carrier lifetime, space charge polarization, and surface degradation. In addition, mercuric iodide is an extremely soft material that is easily damaged by the slight pressure of an electrical connection and by temperatures over sixty degrees Celsius. In general, these compound semiconductors do not interact with neutrons such that they must be coupled with a thin layer of a neutron absorbing material, such as $^6$LiF or $^{10}$B. A reaction between $^6$Li or $^{10}$B occurs in the thin absorber layer, which creates alpha particles that are detected by a semiconducting substrate. The absorber layer must be thin in order for the semiconducting substrate to detect the resultant alpha particles. $^3$He gas filled tube detectors are the state-of-the-art for thermal neutron detection.

As a result, U.S. Pat. No. 7,687,780 (Bell et al.) provides a semiconductor detector of ionizing electromagnetic radiation, neutrons, and energetic charged particles. The detecting element includes a compound having the composition I-III-VI$_2$ or II-IV-V$_2$, where the "I" component is from column 1A or 1B of the periodic table, the "II" component is from column 2B of the periodic table, the "III" component is from column 3A of the periodic table, the "IV" component is from column 4A of the periodic table, the "V" component is from column 5A of the periodic table, and the "VI" component is from column 6A of the periodic table. The detecting element detects ionizing electromagnetic radiation by generating a signal proportional to the energy deposited in the element, and detects neutrons by virtue of the ionizing electromagnetic radiation emitted by one or more of the constituent materials subsequent to capture. The detector may contain more than one neutron sensitive component.

Related to the I-III-VI$_2$ compounds, however, improved methods for combining the elemental constituents in a multistep synthetic process are still required, providing improved purity and homogeneity and more precisely controlling the reaction rate and yielding a I-III-VI$_2$ charge with a single phase stoichiometry.

Further, large arrays of helium-3 gas tubes are currently being used in neutron imaging applications. These neutron imagers can be designed to allow a wide range of incident neutron energies in samples and, as such, require a similarly wide range of neutron energies to be detected. Current and future usage forecasts suggest that helium-3 supplies will not be sufficient to sustain worldwide neutron detection needs, thereby creating a need for alternative materials. LiF-coated semiconductors and scintillators are the leading candidates; however, their neutron efficiency is limited to less than about 20%. Thus, what is still needed in the art is an alternative material that provides much greater neutron efficiency, enhanced sensitivity, enhanced spatial resolution, smaller detector footprint, and lower cost. It should be noted that, thermal and cold neutron imaging is typically conducted at neutron science centers and the like, while fast neutron imaging (i.e. radiography) is typical of nonproliferation and treaty verification and the like.

BRIEF SUMMARY OF THE DISCLOSURE

In various exemplary embodiments, the present disclosure provides a multistep synthetic process for synthesizing an inorganic compound with unique electrical and optical properties. This compound is semiconducting and can be developed for nonlinear optical applications, as well as radiation detection. The I-III-VI$_2$ stoichiometry crystallizes into a chalcopyrite type structure, and when the Group I element is lithium, the material is potentially ideal for the room temperature detection of neutrons, for example. The best known synthesis method, described in U.S. Pat. No. 7,687,780 (Bell et al.), involves heating stoichiometric quantities of the three elemental powders simultaneously to form the I-III-VI$_2$ compound. For the lithium containing compounds, lithium reactivity is difficult to control, leading to poor phase homogeneity. Thus, the present disclosure provides improved methods for combining the elemental constituents in a multistep synthetic process. These methods provide improved purity and homogeneity and more precisely control the reaction rate, thereby yielding a I-III-VI$_2$ charge with a single phase stoichiometry.

In one exemplary embodiment, the present disclosure provides a method for synthesizing I-III-VI$_2$ compounds, including: melting a Group III element; adding a Group I element to the melted Group III element at a rate that allows the Group I and Group III elements to react thereby providing a single phase I-III compound; and adding a Group VI element to the single phase I-III compound and heating. The Group III element is melted at a temperature of between about 200 degrees C. and about 700 degrees C. One (1) mole of the Group I element is added to 1 mole of the Group III element. The Group I element consists of a neutron absorber, preferably $^6$Li, and the Group III element consists of In or Ga. The Group VI element and the single phase I-III compound are heated to a temperature of between about 700 degrees C. and about 1000 degrees C. Two (2) moles of the Group VI element are added to the single phase I-III compound. Preferably, the Group VI element consists of S, Se, or Te. Optionally, the method also includes doping with a Group IV element activator.

In another exemplary embodiment, the present disclosure provides a method for synthesizing I-III-VI$_2$ compounds, including: melting a Group III element; adding a Group I element to the melted Group III element at a rate that allows the Group I and Group III elements to react thereby providing a single phase I-III compound; and adding a Group VI element to the single phase I-III compound under heat while rotating all constituents at an angle. The Group III element is melted at a temperature of between about 200 degrees C. and about 700 degrees C. One (1) mole of the Group I element is added to 1 mole of the Group III element. The Group I element consists of a neutron absorber, preferably $^6$Li, and the Group III element consists of In or Ga. The Group VI element and the single phase I-III compound are heated to a temperature of between about 700 degrees C. and about 1000 degrees C. Two (2) moles of the Group VI element are added to the single phase I-III compound. Preferably, the Group VI element consists of S, Se, or Te. Optionally, the method also includes doping with a Group IV element activator.

In a further exemplary embodiment, the present disclosure provides a method for synthesizing I-III-VI$_2$ compounds, including: melting a Group III element; adding a Group I element to the melted Group III element at a rate that allows the Group I and Group III elements to react thereby providing a single phase I-III compound; and adding a Group VI element to the single phase I-III compound under heat via vapor transport. The Group III element is melted at a temperature of between about 200 degrees C. and about 700 degrees C. One (1) mole of the Group I element is added to 1 mole of the Group III element. The Group I element consists of a neutron absorber, preferably $^6$Li, and the Group III element consists of In or Ga. The Group VI element and the single phase I-III compound are heated to a temperature of between about 700 degrees C. and about 1000 degrees C. Two (2) moles of the Group VI element are added to the single phase I-III compound. Preferably, the Group VI element consists of S, Se, or Te. Optionally, the method also includes doping with a Group IV element activator. In this exemplary embodiment, the single phase I-III compound and the Group VI element are physically separated in the reaction vessel prior to the reaction. The reaction takes place through vapor transport of the Group VI element into the single phase I-III compound melt by maintaining the Group VI element region at a higher temperature than the single phase I-III compound melt region.

In various exemplary embodiments, the present disclosure also provides neutron imaging applications. As alluded to above, the class of Li-containing semiconductor compounds of general composition Li-III-VI$_2$, where III is a Group III element, such as Ga or In, and VI is a Group VI element, such as S, Se, or Te, has been shown to respond to neutrons. The present disclosure applies these neutron detection properties to neutron imaging applications. For example, thermal neutrons can be detected by enriching the $^6$Li isotopes, while high energy neutrons can be detected with the $^7$Li isotopes. The semiconductor crystals are arranged in an array, preferably a pixelated array, with appropriate electronics detecting the resulting electrical charges, offering enhanced sensitivity and spatial resolution as compared to current neutron imaging technologies.

Thus, in a still further exemplary embodiment, the present disclosure provides a neutron imaging system, including: a plurality of Li-III-VI$_2$ semiconductor crystals arranged in an array, wherein III represents a Group III element and VI represents a Group VI element; and electronics operable for detecting a charge in each of the plurality of crystals in the presence of neutrons and for imaging the neutrons. Optionally, the Li is $^6$Li and the neutrons are thermal neutrons. Optionally, the Li is $^7$Li and the neutrons are high energy neutrons. Optionally, the Group III element is one of Ga and In. Optionally, the Group VI element is one of S, Se, and Te. Each of the crystals is formed by: melting the Group III element; adding the Li to the melted Group III element at a rate that allows the Li and Group III element to react, thereby providing a single phase Li-III compound; and adding the Group VI element to the single phase Li-III compound and heating. The Group III element is melted at a temperature of between about 200 degrees C. and about 700 degrees C. One (1) mole of the Li is added to 1 mole of the Group III element. The Group VI element and the single phase Li-III compound are heated to a temperature of between about 700 degrees C. and about 1000 degrees C. Two (2) moles of the Group VI element are added to the single phase Li-III compound. Optionally, each of the crystals is also formed by doping with a Group IV element activator.

Finally, in a still further exemplary embodiment, the present disclosure provides a method for providing a neutron imaging system, including: providing a plurality of Li-III-VI$_2$ semiconductor crystals arranged in an array, wherein III represents a Group III element and VI represents a Group VI element; and providing electronics operable for detecting a charge in each of the plurality of crystals in the presence of neutrons and for imaging the neutrons. Optionally, the Li is $^6$Li and the neutrons are thermal neutrons. Optionally, the Li is $^7$Li and the neutrons are high energy neutrons. Optionally, the Group III element is one of Ga and In. Optionally, the Group VI element is one of S, Se, and Te. Each of the crystals is formed by: melting the Group III element; adding the Li to the melted Group III element at a rate that allows the Li and Group III element to react, thereby providing a single phase Li-III compound; and adding the Group VI element to the single phase Li-III compound and heating. The Group III element is melted at a temperature of between about 200 degrees C. and about 700 degrees C. 1 mole of the Li is added to 1 mole of the Group III element. The Group VI element and the single phase Li-III compound are heated to a temperature of between about 700 degrees C. and about 1000 degrees C. 2 moles of the Group VI element are added to the single phase Li-III compound. Optionally, each of the crystals is also formed by doping with a Group IV element activator.

BRIEF DESCRIPTION OF THE DRAWINGS

The present disclosure is illustrated and described herein with reference to the various drawings, in which like reference numbers are used to denote like method steps/system components, as appropriate, and in which.

DETAILED DESCRIPTION OF THE DISCLOSURE

Figure 1:
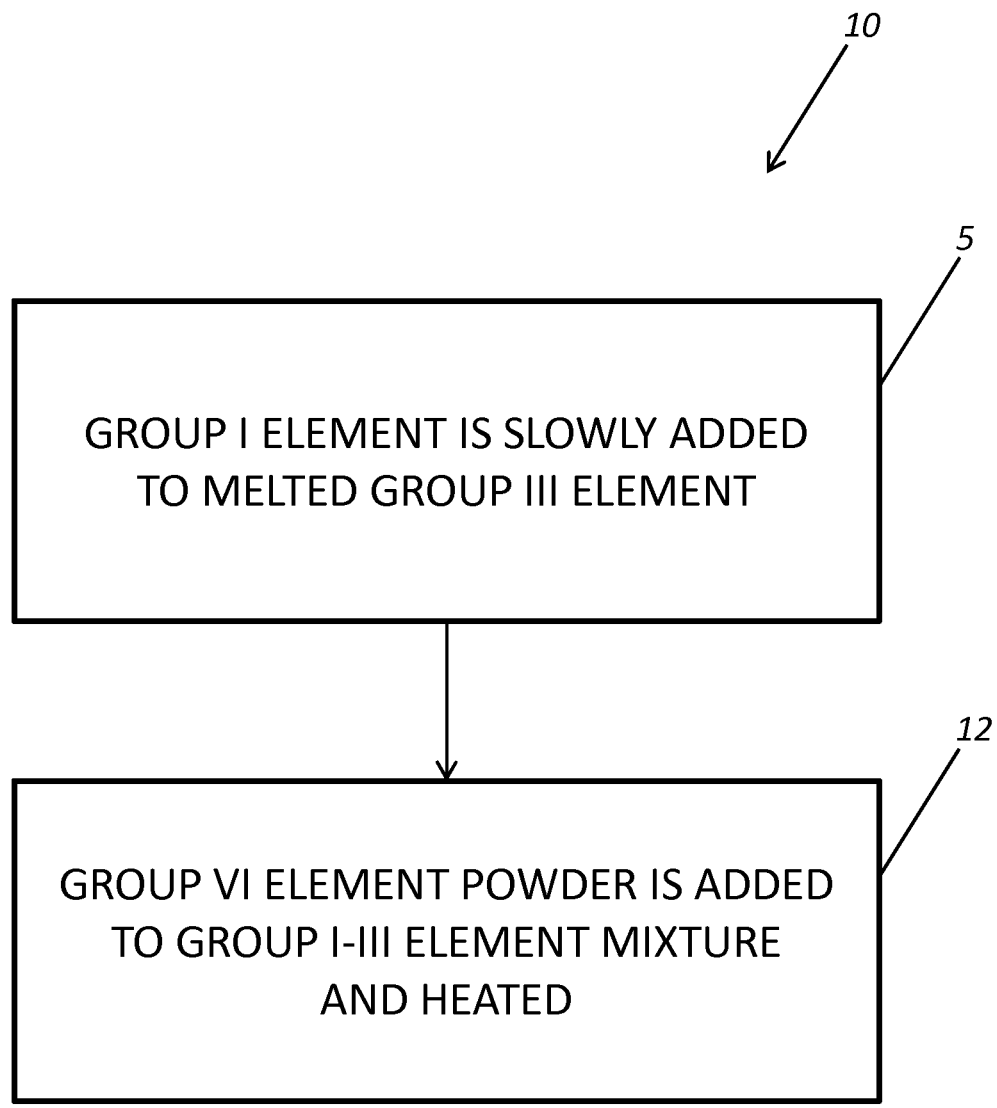
FIG. 1 is a flowchart illustrating one exemplary embodiment of the method for synthesizing I-III-VI$_2$ compounds of the present disclosure, specifically utilizing a heating process.

Again, related to U.S. Pat. No. 7,687,780 (Bell et al.), the detecting element includes a compound having the composition I-III-VI$_2$ or II-IV-V$_2$, where the "I" component is from column 1A or 1B of the periodic table, the "II" component is from column 2B of the periodic table, the "III" component is from column 3A of the periodic table, the "IV" component is from column 4A of the periodic table, the "V" component is from column 5A of the periodic table, and the "VI" component is from column 6A of the periodic table. A more concise manner of description is that the crystal is formed from elements in the group of 1A-3A-6A, 1B-3A-6A, or 2B-4A-5A of the periodic table. An example from group 1A-3A-6A is lithium-gallium-selenium. An example from group 1B-3A-6A is copper-gallium-selenium. An example from group 2B-4A-5A is cadmium-germanium-antimony. Crystals formed from groups 1B-3A-6A and 2B-4A-5A are chalcopyrites. The detecting element detects ionizing electromagnetic radiation by generating a signal proportional to the energy deposited in the element, and detects neutrons by virtue of the ionizing electromagnetic radiation emitted by one or more constituent materials subsequent to capture. The detector may contain more than one neutron sensitive element.

The detecting system generally includes a semiconductor crystal onto which conducting electrodes are deposited on opposing surfaces of the crystal. The semiconductor material may be intrinsic material or doped to produce intrinsic material. Intrinsic material, when referring to semiconductors, refers to a semiconductor material in which the majority and minority charge carriers in the material are balanced and the material does not display either negative (n-) or positive (p-) type conductivity. Doping is the process of introducing small amounts of impurities (typically in the amount of parts per million (ppm)) for the purpose of altering the electrical properties of the material to force a desired density of positive and negative charge carriers. The electrical contacts may be ohmic, or may be Schottky. An ohmic contact is a metal semiconductor contact with very low resistance independent of the polarity of the applied voltage. A Schottky contact is a metal semiconductor contact used to form a potential barrier. The resulting detecting element forms a p-n, or p-i-n diode, or simply a bulk semiconducting material.

In a preferred embodiment, a voltage is applied between the electrodes by a suitable means, such as a battery. A resistor is provided in line between one of the electrodes and the battery. Any signal generated in response to radiation is extracted through a junction between the crystal and the resistor. If the detecting element is simply bulk semiconducting material, then the polarity of the voltage with respect to the resistor is of no consequence. Although the resistor connected between the negative terminal of the battery and the crystal is contemplated, the resistor may also be connected between the positive terminal of the battery and the crystal with the signal taken from the junction between the resistor and the crystal. If the crystal is realized as a diode (p-n, p-i-n, or Schottky), then the connection must be such that the diode is reverse biased by the battery.

When the crystal is exposed to ionizing electromagnetic radiation, electron-hole pairs are created in the bulk of the material. These charges are separated by the applied voltage and the resulting charge pulse is sensed as a current pulse or a voltage pulse. The amplitude of the charge pulse is proportional to the energy deposited in the crystal by the radiation. In this mode, the crystal realizes a detector of alpha, beta, gamma, and x-ray radiation, in addition to cosmic rays.

In one arrangement, the crystal may be fabricated with one element that reacts with neutrons and subsequently emits ionizing electromagnetic radiation. The crystal then also serves to detect neutrons. For example, if the "I" element is silver (Ag), an element from column 1B of the periodic table, then exposure to neutrons results in transmutation of the silver nuclei to radioisotopes with short half-lives. These isotopes decay by the emission of beta particles (electrons), which create ionization in the detector just as would radiation originating outside the detecting element. Analysis of the spectrum of pulse amplitudes and the temporal behavior of the count rate yields a signature of the presence of neutrons.

In another arrangement, if the "I" element is lithium, an element from column 1A of the periodic table, then exposure to neutrons results in the exothermic reaction $^6$Li(n,α)$^3$H. The energetic triton and alpha particles liberate charge as they decelerate, ultimately depositing their entire energy in the crystal. Analysis of the resulting spectrum of pulse amplitudes yields a signature of the presence of neutrons.

In a further arrangement, if the "III" (3A) element of the crystal is indium (In), behavior similar to that described for silver is observed. In a still further arrangement, more than one element may be neutron sensitive. For example, if both silver and indium are used, then multiple half-lives are observed in the count rate, and spectra of beta particles characteristic of both elements are observed in the pulse height spectrum. Analysis of such data can give information on the spectral characteristics of the incident neutron flux.

In operation, the semiconductor radiation detecting apparatus works in the following manner. Means are provided to convert current or charge pulses to a digital value. The electrical charge signal generated in response to radiation passes from the junction through a capacitor to a charge integrating pre-amplifier whose output signal, in turn, is directed to a shaping amplifier. The shaping amplifier produces an approximately Gaussian shaped pulse. The pulse is directed to an analog-to-digital converter (ADC), which translates the analog voltage developed by the shaping amplifier into a digital value. The digital values from the converter are directed to a processor and display. The processor records the number of times each value occurs during a measurement. This accumulates a histogram of the magnitudes of the pulses produced by the incident radiation. The processor compares these values to known values and provides an indication of the incident radiation based on the comparison. The use of the amplifiers, converter, and processor to condition signals and create an indication of the incident radiation is well known to those of ordinary skill in the art and does not require detailed explanation.

In an alternate embodiment, the pre-amplifier simply provides gain without integration and the shaping amplifier is replaced by a voltage comparator and gated integrator. The voltage comparator triggers the gated integrator to integrate the voltage pulse from the pre-amplifier. The gated integrator signals the ADC to perform a conversion when the integration period is complete. The processor and display perform the same functions as described above.

In another alternate embodiment, a battery supplies bias to the crystal. The charge generated by incident radiation in the crystal is separated by the potential developed by the virtual ground at the inverting terminal of the operational amplifier, and the resulting current pulse is forced through a feedback resistor. In this manner, the current pulse is converted to a voltage pulse and is then directed to the pre-amplifier.

These crystals are useful as radiation detectors, and as semiconductors, for the following reasons. Carrier mobility in the range of 500-10,000 cm$^2$/V-s has been reported and band gaps between 1.2 and 2.7 eV have been produced. These values are comparable to or better than those of germanium and indicate that performance at room temperature should exceed that of CZT. In addition, some of the constituent materials have high neutron absorption cross sections, conferring simultaneous sensitivity to ionizing electromagnetic radiation and neutrons.

There are a number of advantages to using chalcopyrites. There is a ready availability of high purity, oriented, crack free, single chalcopyrite crystals produced for use in optical applications. These crystals are used in infrared nonlinear optical equipment to effect second harmonic generation or optical parametric oscillation. The finished materials have improved properties that should continue to improve as a result of research and development spurred by the interest of the military in using chalcopyrites in high powered lasers. Chalcopyrites have physical properties that permit their use as semiconductor radiation detectors at room temperature. As such, they operate according to the same physics as do silicon, CZT, and mercuric iodide. However, they differ from these materials in that the average atomic number is much larger than silicon, making them useful at higher energies than silicon. They can be grown in large, crack free single crystal boules (unlike CZT and mercuric iodide). They also are an improvement over mercuric iodide in that the use of mercuric iodide is limited to applications in which the temperature does not exceed 80 degrees Celsius, while chalcopyrites can withstand temperatures up to several hundred degrees Celsius.

Without limitation, it may be advantageous to deposit more than two electrodes onto the crystal to control the shape of the internal electric field. In another example, sandwiching the crystal between spring loaded contacts enables the application of a voltage without the deposition of electrodes. In yet another example, the pre-amplifier, shaping amplifier, and ADC may be replaced by a charge-to-digital converter.

Figure 2:
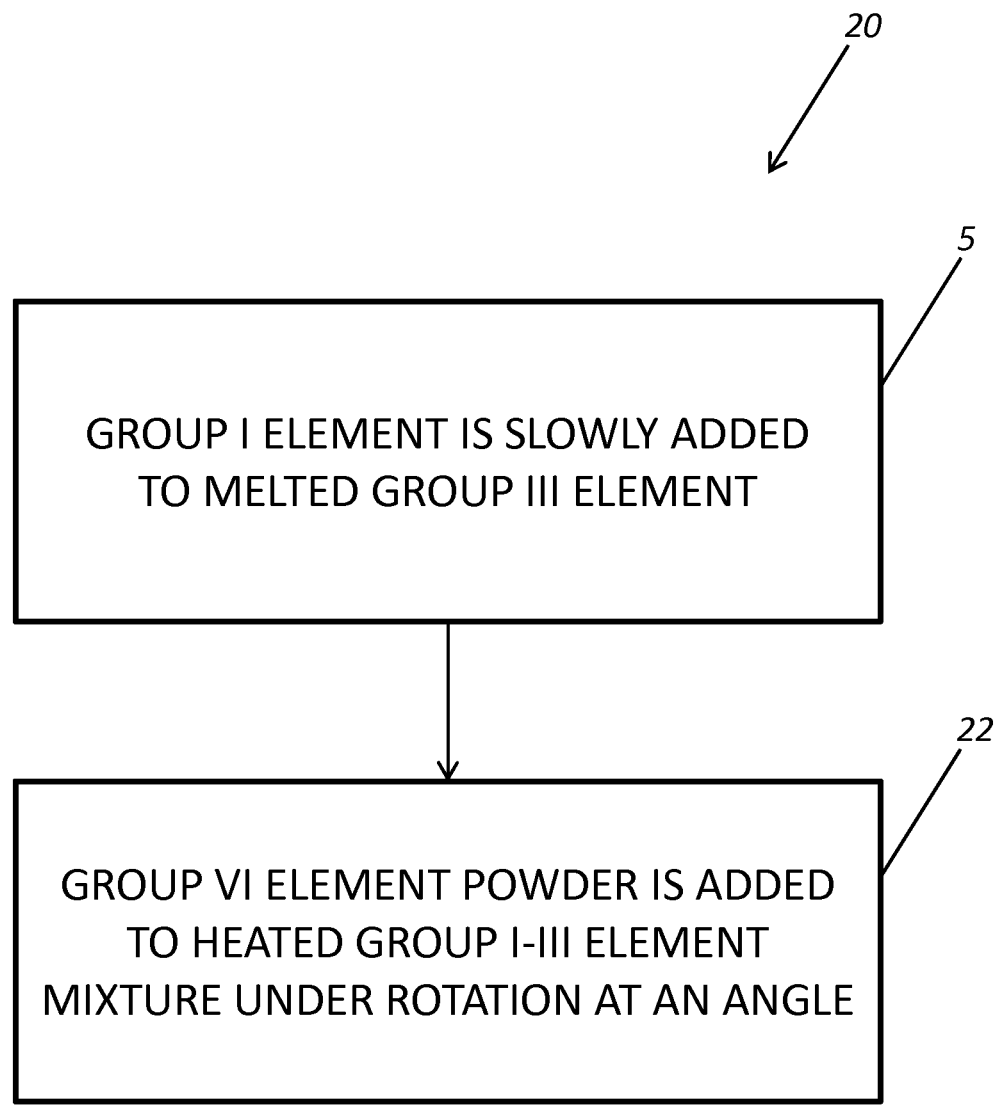
FIG. 2 is a flowchart illustrating another exemplary embodiment of the method for synthesizing I-III-VI$_2$ compounds of the present disclosure, specifically utilizing a mixing process.
Figure 3:
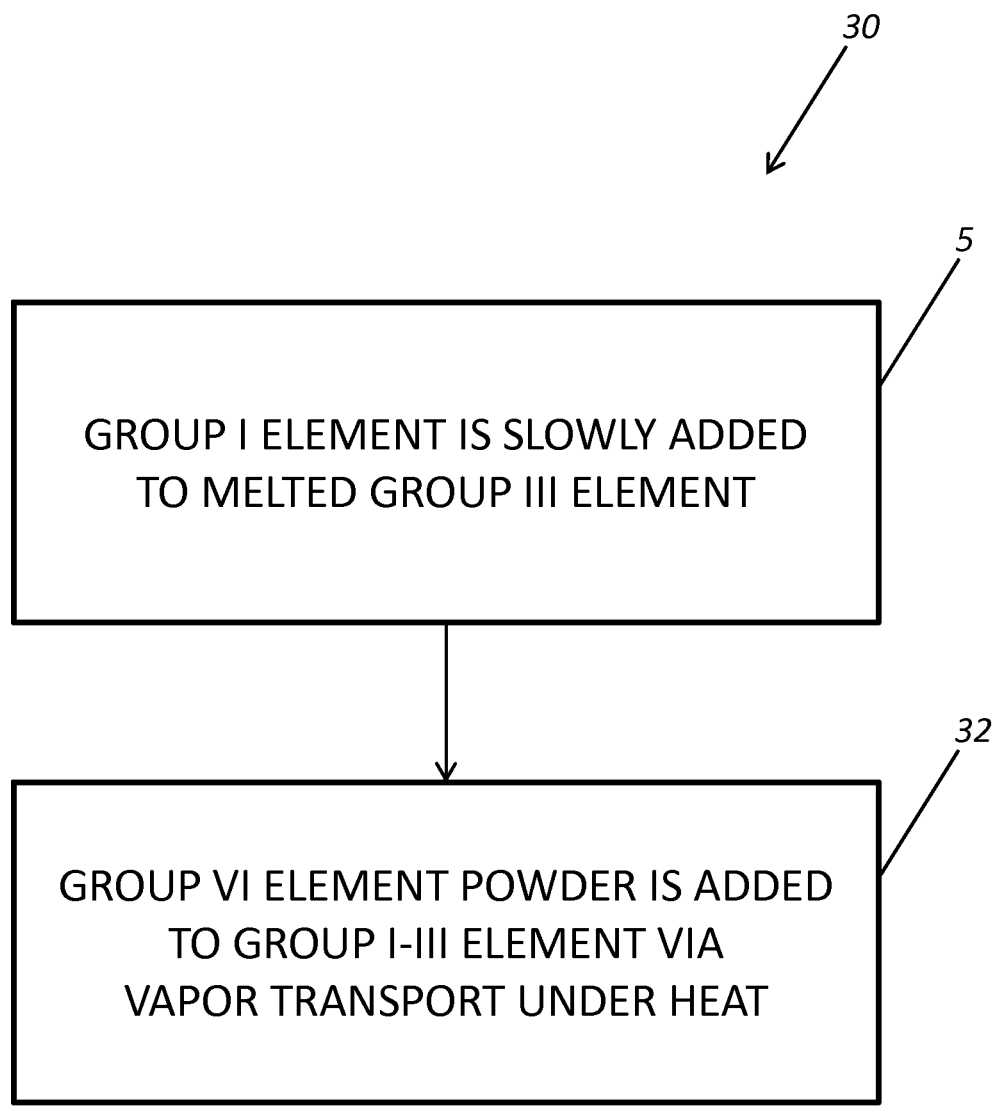
FIG. 3 is a flowchart illustrating a further exemplary embodiment of the method for synthesizing I-III-VI$_2$ compounds of the present disclosure, specifically utilizing a vapor transport process.

In view of the above, the present disclosure involves separating I-III-VI$_2$ synthesis from the constituent elements into two distinct steps, and three associated embodiments are contemplated. The highest quality elemental starting materials are required to achieve successful synthesis of I-III-VI$_2$ compounds. Group I elements typically have the lowest purities as starting materials. Referring to FIGS. 1-3, in all exemplary embodiments, the most reactive element (Group I) is reacted with the Group III element, forming a binary alloy with equal stoichiometry (step 5). The Group III element is melted in a crucible under inert atmosphere for increased purity and safety. The Group I element is then slowly added to the melt, allowing the small amount of Group I element to react before another addition. This process minimizes overheating of the reaction, which causes additional alloy stoichiometries to form in the melt. The result is a highly crystalline, single phase I-III material. Two moles of a Group VI element are then added to the I-III compound at elevated temperature to form the chalcopyrite I-III-VI$_2$. The method by which the Group VI element is added is different in each of the three exemplary embodiments.

Referring specifically to FIG. 1, in the first exemplary embodiment 10, the Group VI elemental powder is added directly to the I-III alloy and heated to 700-900 degrees C. (depending on the group VI element) in a crucible (step 12). The reaction is allowed to proceed to completion and then cooled. Because the I-III compound is formed in an initial reaction step, the stoichiometry is defined as one mole for each element. Addition of the Group VI element for the final I-III-VI reaction has lower overall stoichiometric variability throughout the charge.

Referring specifically to FIG. 2, in the second exemplary embodiment 20, the addition of the Group VI element into a single crucible is as with the first exemplary embodiment; however, the constituents are mixed at elevated temperature with constant crucible rotation at an angle (step 22), for example about 20 degrees. Rotation further promotes mixing during the synthesis to reduce phase variability.

Referring specifically to FIG. 3, the third exemplary embodiment 30 involves vapor transport of the Group VI element (step 32). The previously prepared I-III compound is placed in one well of a crucible, while the Group VI element is placed in an adjacent well. As the mixture is heated to 700-900 degrees C., the Group VI element slowly vaporizes and is transported through thermal currents to the melted group I-III well. The reaction then occurs to form I-III-VI$_2$. Vapor transport further slows the reaction to minimize overheating and promote a single phase synthetic charge.

It should be noted that the methods of the present invention are not limited to the synthesis of semiconductor materials. Doping with an activator (e.g., Group IV element) may be performed to create a scintillator material, for example.

Figure 4:
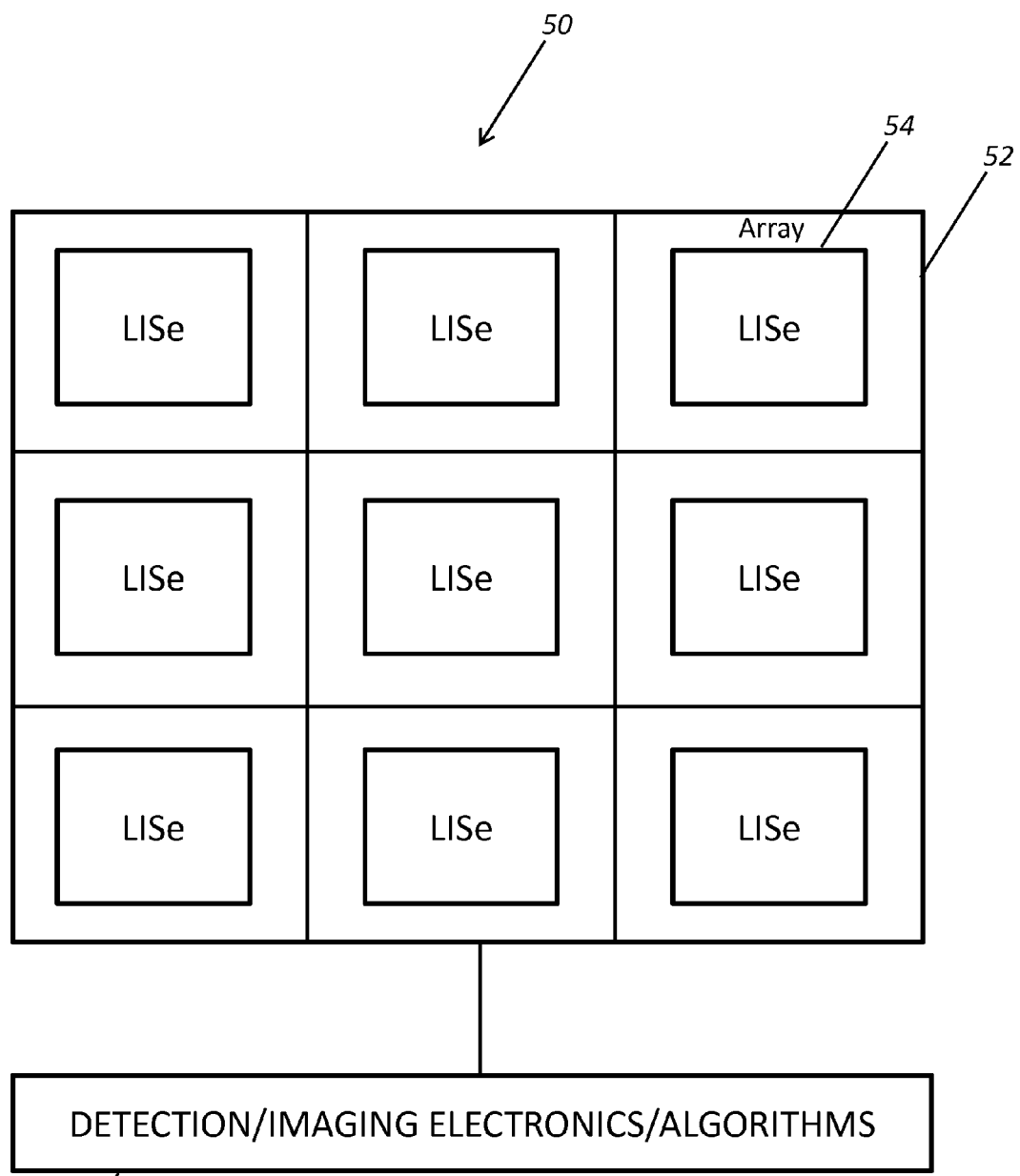
FIG. 4 is a schematic diagram illustrating one exemplary embodiment of the neutron imaging system of the present disclosure, the neutron imaging system utilizing Li-containing semiconductor compounds of general composition Li-III-VI$_2$, as described herein.

Referring now specifically to FIG. 4, in one exemplary embodiment of the neutron imaging system 50 of the present disclosure, the neutron imaging system 50 includes an array 52 of Li chalcopyrite crystals 54 synthesized by the methods described above. This array 52 may include any number of Li chalcopyrite crystals 54 (greater than one) arranged in any required manner. Appropriate electronics 56 are coupled to the array 52, and typically include a VME rack, preamplifiers, a power module, digitizers, etc. The algorithm for querying the array of Li chalcopyrite crystals 54 includes processing the generated electrical signal of each spatial location of the crystals 54 using a conventional MCA or CT software.

As described above, the class of Li-containing semiconductor compounds of general composition Li-III-VI$_2$, where III is a Group III element, such as Ga or In, and VI is a Group VI element, such as S, Se, or Te, respond to neutrons. $^6$LiInSe$_2$ provides the best neutron response to thermal neutrons, for example. In other disclosures that are continuations of U.S. patent application Ser. No. 13/658,591, the crystal is applied to simple neutron counting applications, where a single crystal is electrically biased such that a neutron generates enough charged particles within the crystal to create detectable current. The present disclosure, however, relates to the application of such an Li-III-VI$_2$ crystal in an electrically isolated, pixelated array in order to generate a neutron response map. The application of computed tomography (CT) algorithms transforms the spatially specific neutron response to generate an image of the sample being interrogated. The neutron contrast image of a particular projection of a sample is compiled via digital geometric processing to create a three-dimensional (3D) projection of the sample. Thermal neutrons can be detected by enriching the $^6$Li isotopes within the crystal, while high energy neutrons can be detected with the $^7$Li isotopes. The same synthesis and growth parameters are used to prepare the Li-III-VI$_2$ crystal regardless of the Li isotope used. This makes the growth of this crystal uniform for all imaging applications, thus simplifying the process. Crystals can be cut and assembled into a wide range of arrays depending of the desired sensitivity and spatial resolution. Exemplary applications, shapes, and array configurations include a single plate of pixelated crystals or a set of two pixelated crystal plates at a known offset.

Again, there are a few semiconductor and scintillator technologies being developed as alternatives to helium-3 or $^{10}$BF$_3$ gas tubes for thermal neutron detection, wherein the neutron either creates an electrical or light response that is detected. However, these alternative technologies have shortcomings that are overcome by the present disclosure. Gas tube detector arrays are the most common detector currently; however, such detectors can only achieve increased spatial resolution by increasing the distance between the detector bank and the sample. In contrast, Li-III-VI$_2$ can achieve the same spatial resolution in closer proximity to the sample. While LiF coated scintillators have shown high spatial resolution, they suffer from low neutron detection efficiency. Thus, both of these alternative technologies are supplanted by that of the present disclosure.

The array 52 is selected based on the desired sensitivity, energy resolution, and spatial resolution, as well as the neutron energy from the source. Exemplary embodiments include, but are not limited to:

1. A checkerboard arrangement with alternating $^6$LI and $^7$Li crystals (i.e., $^6$Li-III-VI$_2$ and $^7$Li-III-VI$_2$). This would be designed to detect both fast and slow (i.e., thermal) neutrons with reasonable spatial resolution simultaneously. Each crystal would be an individual pixel, for example; or 2. A pixelated array of $^6$Li-III-VI$_2$ crystals in a plane with multiple stacked planes. Each layer gives an x-y location, but combining it with multiple layers of crystals would give direction of the incoming radiation through coincidence. This could be used for computed tomography, for example.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A neutron imaging system, comprising:
    a plurality of Li-III-VI$_2$ semiconductor crystals arranged in an array, wherein III represents a Group III element and VI represents a Group VI element; and
    electronics operable for detecting a charge in each of the plurality of crystals in the presence of neutrons and for imaging the neutrons;
    wherein the Li comprises $^6$Li and the neutrons comprise thermal neutrons or the Li comprises $^7$Li and the neutrons comprise high energy neutrons.

2. The neutron imaging system of claim 1, wherein the Group III element comprises one of Ga and In.

3. The neutron imaging system of claim 1, wherein the Group VI element comprises one of S, Se, and Te.

4. The neutron imaging system of claim 1, wherein each of the crystals is formed by:
    melting the Group III element;
    adding the Li to the melted Group III element at a rate that allows the Li and Group III element to react, thereby providing a single phase Li-III compound; and
    adding the Group VI element to the single phase Li-III compound and heating.

5. The neutron imaging system of claim 4, wherein the Group III element is melted at a temperature of between about 200 degrees C. and about 700 degrees C.

6. The neutron imaging system of claim 4, wherein 1 mole of the Li is added to 1 mole of the Group III element.

7. The neutron imaging system of claim 4, wherein the Group VI element and the single phase Li-III compound are heated to a temperature of between about 700 degrees C. and about 1000 degrees C.

8. The neutron imaging system of claim 4, wherein 2 moles of the Group VI element are added to the single phase Li-III compound.

9. The neutron imaging system of claim 4, further comprising doping with a Group IV element activator.

10. The neutron imaging system of claim 1, wherein the array comprises a pixelated array.

11. A method for providing a neutron imaging system, comprising:
    providing a plurality of Li-III-VI$_2$ semiconductor crystals arranged in an array, wherein III represents a Group III element and VI represents a Group VI element; and
    providing electronics operable for detecting a charge in each of the plurality of crystals in the presence of neutrons and for imaging the neutrons;
    wherein the Li comprises $^6$Li and the neutrons comprise thermal neutrons or the Li comprises $^7$Li and the neutrons comprise high energy neutrons.

12. The neutron imaging method of claim 11, wherein the Group III element comprises one of Ga and In.

13. The neutron imaging method of claim 11, wherein the Group VI element comprises one of S, Se, and Te.

14. The neutron imaging method of claim 11, wherein each of the crystals is formed by:
    melting the Group III element;
    adding the Li to the melted Group III element at a rate that allows the Li and Group III element to react, thereby providing a single phase Li-III compound; and adding the Group VI element to the single phase Li-III compound and heating.

15. The neutron imaging method of claim 14, wherein the Group III element is melted at a temperature of between about 200 degrees C. and about 700 degrees C.

16. The neutron imaging method of claim 14, wherein 1 mole of the Li is added to 1 mole of the Group III element.

17. The neutron imaging method of claim 14, wherein the Group VI element and the single phase Li-III compound are heated to a temperature of between about 700 degrees C. and about 1000 degrees C.

18. The neutron imaging method of claim 14, wherein 2 moles of the Group VI element are added to the single phase Li-III compound.

19. The neutron imaging method of claim 14, further comprising doping with a Group IV element activator.

20. The neutron imaging method of claim 11, wherein the array comprises a pixelated array.

21. A neutron detection and imaging method, comprising:
providing a plurality of Li-III-VI$_2$ semiconductor crystals arranged in an array, wherein III represents a Group III element and VI represents a Group VI element; and
detecting and imaging neutrons using the array;
wherein the Li comprises $^6$Li and the neutrons comprise thermal neutrons or the Li comprises $^7$Li and the neutrons comprise high energy neutrons.

22. The neutron detection and imaging method of claim 21, wherein detected neutrons are imaged using a computed tomography technique.

* * * * *